United States Patent [19]

Clemens

[11] 4,151,845
[45] May 1, 1979

[54] BLOOD GLUCOSE CONTROL APPARATUS

[75] Inventor: Anton H. Clemens, Elkhart, Ind.

[73] Assignee: Miles Laboratories, Inc., Elkhart, Ind.

[21] Appl. No.: 854,508

[22] Filed: Nov. 25, 1977

[51] Int. Cl.² .......................... A61M 5/00; A61B 5/00
[52] U.S. Cl. ............................. 128/214 E; 128/214 R; 128/DIG. 13
[58] Field of Search ........... 128/214 R, 214 E, 214 F, 128/DIG. 12, DIG. 13, 213

[56] References Cited

U.S. PATENT DOCUMENTS

| | | | |
|---|---|---|---|
| 3,837,339 | 9/1974 | Aisenberg et al. | 128/213 |
| 4,003,379 | 1/1977 | Ellinwood | 128/214 E X |
| 4,006,743 | 2/1977 | Kowarski | 128/214 R |
| 4,008,717 | 2/1977 | Kowarski | 128/214 R |
| 4,073,292 | 2/1978 | Edelman | 128/214 E |
| 4,077,405 | 3/1978 | Haerten et al. | 128/214 F |

Primary Examiner—Robert E. Bagwill
Attorney, Agent, or Firm—Roger N. Coe

[57] ABSTRACT

Apparatus is described for controlling blood glucose concentration in a subject by selected infusion of insulin into the blood stream of such subject, depending upon the general blood glucose concentration. This apparatus comprises in combination sensor means for determining the blood glucose concentration and for providing computer input signals based on such measurement, computer means for receiving such input signals and for providing output signals based upon such input signals, and pump means responsive to such computer output signals to supply insulin to such subject at a rate determined by such output signals. The computer means is programmed to derive the output signals in accordance with specific equations employing certain independently selected values relating to basal blood glucose concentrations and basal insulin infusion rates at such basal blood glucose concentrations.

13 Claims, 14 Drawing Figures

BLOOD GLUCOSE CONTROL APPARATUS

FIELD OF THE INVENTION

The present invention relates to glucose monitoring systems in general, and more particularly to apparatus for controlling blood glucose concentrations in a subject by selected infusion of insulin.

BACKGROUND OF THE INVENTION

Insulin is a hormone produced in the pancreas which is essential for the proper metabolism of glucose in the blood. The failure to produce insulin in appropriate quantities results in the onset of diabetes mellitus.

Since the early 1900's diabetic conditions have been treated by periodic injections of insulin, coupled with diet and exercise control. It was initially felt that such treatment could be used to completely control a diabetic condition. It is difficult, however, to avoid over or under compensation since insulin injection generally cannot be timed to coincide with carbohydrate intake. Situations thus exist in which the amount of insulin present is either in excess of or less than that required to handle the specific blood glucose level at any given time. Such situations are especially severe when an individual with a diabetic condition is under stress conditions, such as surgery or during childbirth.

It is generally recognized that individuals do not respond uniformly to insulin treatments and that some patients are better managed by short acting (regular or Semilente) insulin which requires several injections per day, whereas other patients are better managed with intermediate (globin, NPH or Lente) or longer acting (protamine zinc or Ultralente) insulin which require less frequent injections. Neither the short nor the longer acting varieties of insulin is capable of regulating a patient's blood glucose concentration accurately on a minute-to-minute basis because of varying demands created by food and exercise. Only by following a life of balanced diet and exercise can a patient prevent sudden and excessive changes in the requirements for insulin. Such a regimen will maintain the patient's blood glucose concentration below an acceptable upper level, thereby limiting the possibility of hyperglycemia, and above a safe lower limit, thereby limiting the possibility of hypoglycemia. Unfortunately, a dangerously low blood glucose concentration can also result from the use of larger infusions of insulin to counteract a rising concentration of blood glucose. This is because there is an overshoot when the concentration of blood glucose ceases to increase or actually decreases and the presence of the insulin causes a rapid decline in blood glucose concentration to a concentration below the safe limit. The resulting hypoglycemia can be fatal in some cases.

Various systems and apparatus have been proposed to analyze the blood glucose concentration and to infuse insulin or glucose based upon such analysis in an effort to control the blood glucose level within desired ranges. One approach, referred to as the limit approach, continuously monitors a patient's blood glucose concentration and regulates this concentration by administering insulin when the concentration reaches an upper limit and administering dextrose when the blood glucose concentration reaches a lower limit. The limit approach, however, has several difficulties because it is possible to overshoot both the upper and lower limits. The system is not capable of controlling sudden changes in blood glucose concentration. Another approach is to use proportional regulation by solely matching the infusion rate of insulin to the blood glucose concentration according to a linear relationship. Here again, hypoglycemia can result if there is a large requirement for insulin followed by a natural reduction in the blood glucose concentration.

Still another approach is described in *Diabetes* 23(5), 389–404 (1974) in which apparatus is described having a computer which operates an infusion pump to infuse insulin or glucose based upon analytical blood glucose values. The computer derives its output signal for pump operation from algorithms based on hyperbolic tangential functions. While this prior art computer control has advantages, it also has the distinct disadvantage that the responses obtained do not always satisfactorily provide adequate control. In addition, the apparatus provides only limited flexibility in the selection of specific operating conditions for particular individuals whose blood glucose concentrations are being controlled by the apparatus.

The development of a rapid glucose analyzer with a total response time of less than two minutes has significantly affected the systems and apparatus being used. It is no longer necessary to calculate and use a predicted glucose value based on an averaging of previous glucose values, whether the average is an arithmetic mean or weighted average, in order to compensate for a long analyzer lag time because the response time of a rapid analyzer approximates the physiological response of a healthy subject. This fact has permitted improved apparatus for monitoring and controlling blood glucose levels to be developed.

SUMMARY OF THE INVENTION

An object of the present invention is to provide apparatus for accurately monitoring the blood glucose level in a subject.

Another object of the present invention is to provide apparatus for very accurately controlling the amount of insulin supplied to a subject based upon an algorithm-controlled computer signal.

Still another object of the present invention is to provide insulin infusion apparatus which has a high degree of flexibility in the selection of specific operating conditions for the particular subject whose blood glucose concentrations are being controlled by the apparatus.

In accordance with the present invention, apparatus is provided for controlling the concentration of glucose in the blood stream of a subject by controlled infusion of insulin to the subject dependent upon the concentration of glucose in the subject's blood stream, such apparatus comprising in combination means for determining serial values of blood glucose concentration in the blood stream of a subject and for providing computer input signals corresponding to said serial values; computer means connected to said first mentioned means and operable to provide output signals in response to the said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the following equation:

$$IR = RI\left(\frac{G - BI}{QI} + 1\right)^n + K\frac{dG}{dt}$$

wherein: IR = insulin infusion rate,
RI = required basal infusion rate at BI,
G = the last glucose value,
BI = the desired basal or steady state glucose concentration,
QI = is a preselected value dependent upon the subject,
K = is a preselected value dependent upon the subject and whether or not the blood glucose concentration of the subject is rising ($K_R$) or falling ($K_F$).
t = time, and
n = a number ranging from 1 to 3

BRIEF DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

The apparatus forming the subject matter of the present invention for controlling the concentration of glucose in the blood stream of a subject by controlled supply of insulin to the subject dependent upon the rate of change of glucose concentration in said blood stream is characterized by means for determining serial values of blood glucose concentration in the blood stream of a subject and for providing computer input signals corresponding to said serial values; computer means coupled to said first-mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the following equation:

$$IR = RI\left(\frac{G - BI}{QI} + 1\right)^n + K\frac{dG}{dt}$$

wherein: IR = insulin infusion rate,
RI = required basal infusion rate at BI,
G = the last glucose value,
BI = the desired basal or steady state glucose concentration,
QI = is a preselected value dependent upon the subject,
K = is a preselected value dependent upon the subject and whether or not the blood glucose concentration of the subject is rising ($K_R$) or falling ($K_F$),
t = time, and
n = a number ranging from 1 to 3

Figure 1:
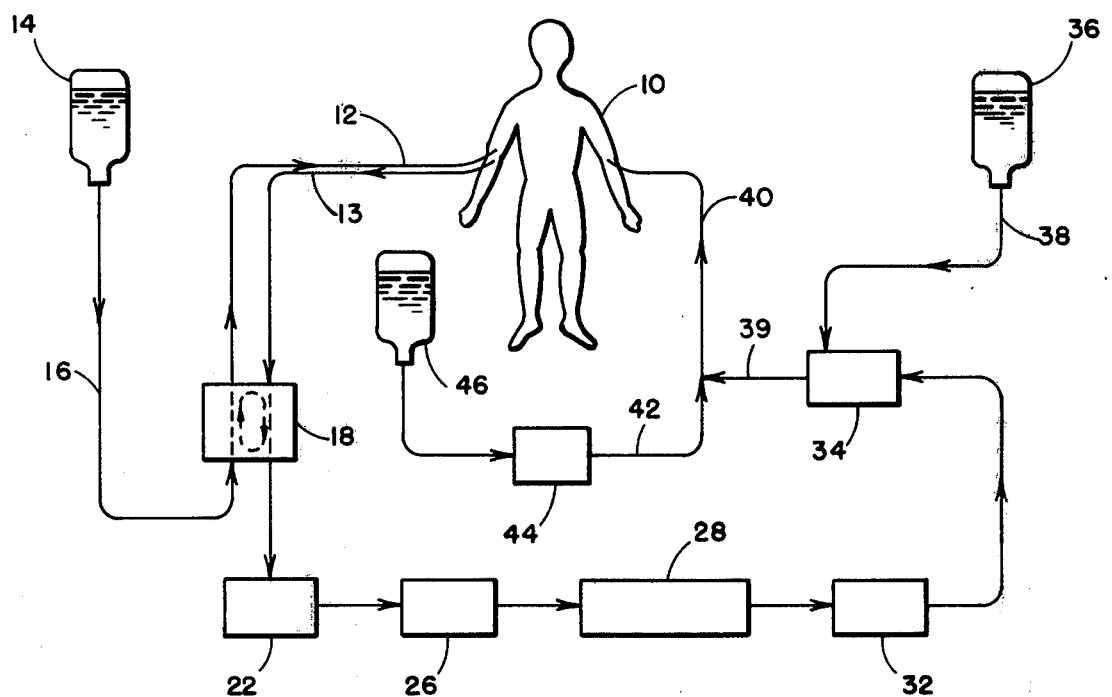
FIG. 1 is a schematic view of apparatus according to the invention coupled to a diabetic subject.

As shown schematically in FIG. 1, blood is removed from the blood stream of subject 10 by suitable means, such as through a double lumen catheter (not shown), which also introduces an anticoagulant such as heparin, in line 12, which is mixed with the blood as it leaves the subject, thereby diluting the blood passing through line 13. The anticoagulant is stored in reservoir 14 and is pumped to the catheter through lines 16 and 12 by suitable means, such as peristaltic pump 18, which also pumps diluted blood from the catheter through line 13 in the opposite direction. Pump 18 runs continuously to drive the diluted blood from line 13 into glucose analyzer 22.

Glucose analyzer 22 can take a variety of forms. For example, using a colorimeter approach, diluted blood enters analyzer 22 and is diluted further with a physiological saline solution before being segmented with air into discrete bits to be dialyzed against a glucose oxidase-peroxidase-chromagen reagent. The presence of blood glucose specifically alters the color of the reagent and the optical density of the resulting color is measured by a colorimeter which generates a corresponding output signal. The resulting signal is then fed to analog-to-digital converter 26 which prepares the input signal for digital computer 28.

In a preferred embodiment glucose analyzer 22 is a membrane type polarographic assembly which measures the glucose level of the diluted blood and generates a corresponding signal which is supplied to analog-to-digital converter 26 which prepares the input signal for digital computer 28. Suitable membrane type polarographic apparatus is described, for example, in U.S. Ser. No. 683,807, filed May 6, 1976 (now U.S. Pat. No. 4,092,233). In this U.S. application a membrane is disclosed containing glucose oxidase which converts glucose to hydrogen peroxide which is detected in the polarographic assembly by a difference in electrical potential.

Analog-to-digital converter 26 feeds the digital input signal corresponding to the blood glucose level to computer 28, which is programmed according to an algorithm which will be discussed later. Responsive to the signals from analyzer 22, the computer determines the infusion rate of insulin for the subject by use of the algorithm programmed into the computer. Once the infusion rate required by the subject has been determined, digital signals are fed from computer 28 to pump interface 32 which controls the infusion pumping which will now be described. Pump 34 connected to interface 32 receives insulin from reservoir 36 by way of line 38 and feeds the insulin into lines 39 and 40. Line 42 receives saline solution from pump 44, which draws said solution from reservoir 46. Accordingly, insulin from reservoir 36 is mixed with saline solution as it is fed into line 40, and the resulting solution is introduced into the blood stream of subject 10 through a suitable catheter (not shown). A closed loop is therefore provided which includes subject 10.

It will be understood that while the use of a digital computer is preferred, converter 26 and computer 28 can be replaced by an analog computer, if desired. Pump 34 would then be driven in analog fashion rather than in digital fashion.

As will be apparent, the regulation afforded by the structure described with reference to FIG. 1 depends on computer algorithms programmable into computer 28. Ideally, the algorithms should be capable of interpreting requirements for insulin to the point where the blood glucose concentration of a subject is maintained substantially constant at a level which is considered normal for the subject in question. An insulin dependent diabetic requires a static insulin release supplemented by a dynamic control function.

Algorithms have been developed which allow investigators to use the present system for:

(1) Static control—a control mode of operation in which insulin release is dependent upon the static value of the blood glucose level;

(2) Dynamic control—a control mode in which insulin infusion is controlled solely by the rate of change of blood glucose levels; and (3) Static plus Dynamic Control—a control mode in which dynamic control and static control are combined for controlling insulin infusion.

During the development of the control algorithms the static control has been optimized so that an elevated glucose level can be reduced asymptotically into the normal range without overshooting into the hypoglycemic state. Furthermore, the static control alogrithm allows control constants to be selected directly for the area of physiological significance, such as the basal insulin infusion rate, the glucose level at which the basal rate should occur, and the "gain" of the control function, as expressed by the expression:

$$RI \left( \frac{G - BI}{QI} + 1 \right)^n$$

Thus, in contrast to earlier control algorithms using the "tangens hyperbolicus", the static control algorithm of the present invention does not have control constants selected primarily to relate to the central portion of the control curve and only secondarily to the critical control region around and slightly above the physiological range. Moreover, instead of maintaining fixed relationships for the dynamic control conditions, the present system utilizes separate control constants during dynamic control for increasing and decreasing blood glucose levels.

In the past, simple averaging of the most recent blood glucose concentration value (BG) readings was used to predict the next BG value. Simple averaging, however, has not provided satisfactory results. Unsatisfactory results have also been obtained when attempts have been made to predict a BG value by using a weighted scale in which a number of previous BG signals received by the computer are weighted with the greatest weight being applied to the last reading.

As indicated, the apparatus of the present invention is capable of operating in several modes at the choice of the operator. In the first or so-called static control mode, insulin is infused into the blood stream of a subject at a rate dependent upon the static value of the blood glucose concentration. In this first mode of operation the computer is programmed to provide, in response to the serial input signals, output signals causing infusion of insulin at a rate derived in accordance with the equation:

$$IR = RI \left( \frac{G - BI}{QI} + 1 \right)^n$$

wherein IR=the insulin infusion rate,
RI=the required basal insulin infusion rate at BI,
G=the last glucose value,
BI=the desired basal (steady state) glucose concentration,
QI=a preselected value depending upon the subject, and
n=a number ranging from 1 to 3

In order to obtain an accurate value and simultaneously to avoid the "noise" due to small minute-to-minute analyzer output fluctuations, a preferred algorithm of the present invention has been developed using a least squares regression line. For this preferred embodiment the slope (m) for five consecutive glucose values $G_0$ to $G_4$, with $G_0$ being the most recent glucose value, becomes:

$$m = (2G_0 + G_1 = G_3 - 2G_4)/10$$

and the value of the last glucose value (Gy), corrected to fit the regression line, becomes:

$$Gy = 2m + (G_0 + G_1 + G_2 + G_3 + G_4)/5$$

Substituting Gy for G the preferred equation for the first mode becomes:

$$IR = RI \left( \frac{Gy - BI}{QI} + 1 \right)^n$$

In the second or dynamic control mode of operation, insulin is infused at a rate dependent solely upon the rate of change of blood glucose levels, and the computer is programmed to provide, in response to the serial input signals, output signals causing infusion of insulin at a rate derived in accordance with the equation:

$$IR = K(dG/dt)$$

wherein IR=the insulin infusion rate,
K=a preselected value dependent upon the subject and whether or not the blood glucose concentration of the subject is rising ($K_R$) or falling ($K_F$),
G=the last glucose value, and
t=time This equation is modified in a preferred embodiment to incorporate the slope of the least squares regression line fit for the most recent blood glucose values to become:

$$IR = Km$$

When this equation is modified to incorporate a factor proportional to the difference between the actual and desired glucose level the equation becomes $IR=Km(G-BI)$ except when G is less than BI, in which event IR equals zero. Using Gy instead of G the final preferred equation for the second mode becomes:

$$IR = Km(Gy-BI)$$

except when Gy is less than BI, in which event IR equals zero. For computational convenience this equation can be written as follows:

$$IR = (Km/10)(Gy-BI)$$

by also increasing the values of K by a factor of 10.

In the third or static plus dynamic control mode of operation, insulin is infused at a rate dependent upon both the first and second modes and the computer is programmed to provide, in response to the serial input signals, output signals causing infusion of insulin at a rate derived in accordance with the equation:

$$IR = RI\left(\frac{G-BI}{QI} + 1\right)^n + K\frac{dG}{dt}$$

and preferably:

$$IR = RI\left(\frac{Gy-BI}{QI} + 1\right)^n + Km(Gy-BI)$$

except when Gy is less than BI, in which event said rate is derived in accordance with the equation:

$$IR = RI\left(\frac{Gy-RI}{QI} + 1\right)^n$$

wherein: IR=insulin infusion rate,
RI=required basal infusion rate at BI,
Gy=the last glucose value, corrected to fit a least squares regression line,
BI=the desired basal (steady state) glucose concentration,
QI=is a preselected value dependent upon the subject,
K=is a preselected value dependent upon the subject and whether or not the blood glucose concentration of the subject is rising ($K_R$) or falling ($K_F$),
m=is the slope of the least squares regression line fit for the most recent consecutive blood glucose values, such as the last five blood glucose values, and
n=a number ranging from 1 to 3

In the above equations IR and RI are expressed in milliunits of insulin per minute of infusion. BI and QI are expressed in milligram percent of glucose. This can also be expressed as milligrams per deciliter (mg/dl). BI represents a selected or desired basal blood glucose concentration which typically would be present in a normal subject under resting conditions. RI represents the required basal insulin infusion rate provided by the body of a normal subject under such conditions and is typically about 10 milliunits per minute for a person having 50 kilograms of body weight. Thus, when the apparatus of the present invention is used with a 70 kilogram human subject, for example, RI is typically about 14 milliunits of insulin per minute. BI is about 80 milligram per deciliter glucose. A nominal QI is about 30 mg/dl of glucose with QI values ranging from about 5 to about 30. K will have a nominal value ($K_R$) of approximately 30 when the blood glucose level is rising and a nominal value ($K_F$) of approximately 8 when the glucose level is falling, if the expression $(Km/10)(Gy-BI)$ is used.

It has been determined that in order to prevent any excess infusion of insulin in hyperglycemic conditions the infusion rates for insulin should have a controlled maximum value. A maximum insulin infusion rate of about 500 milliunits per minute or less has been found suitable.

Figure 2:
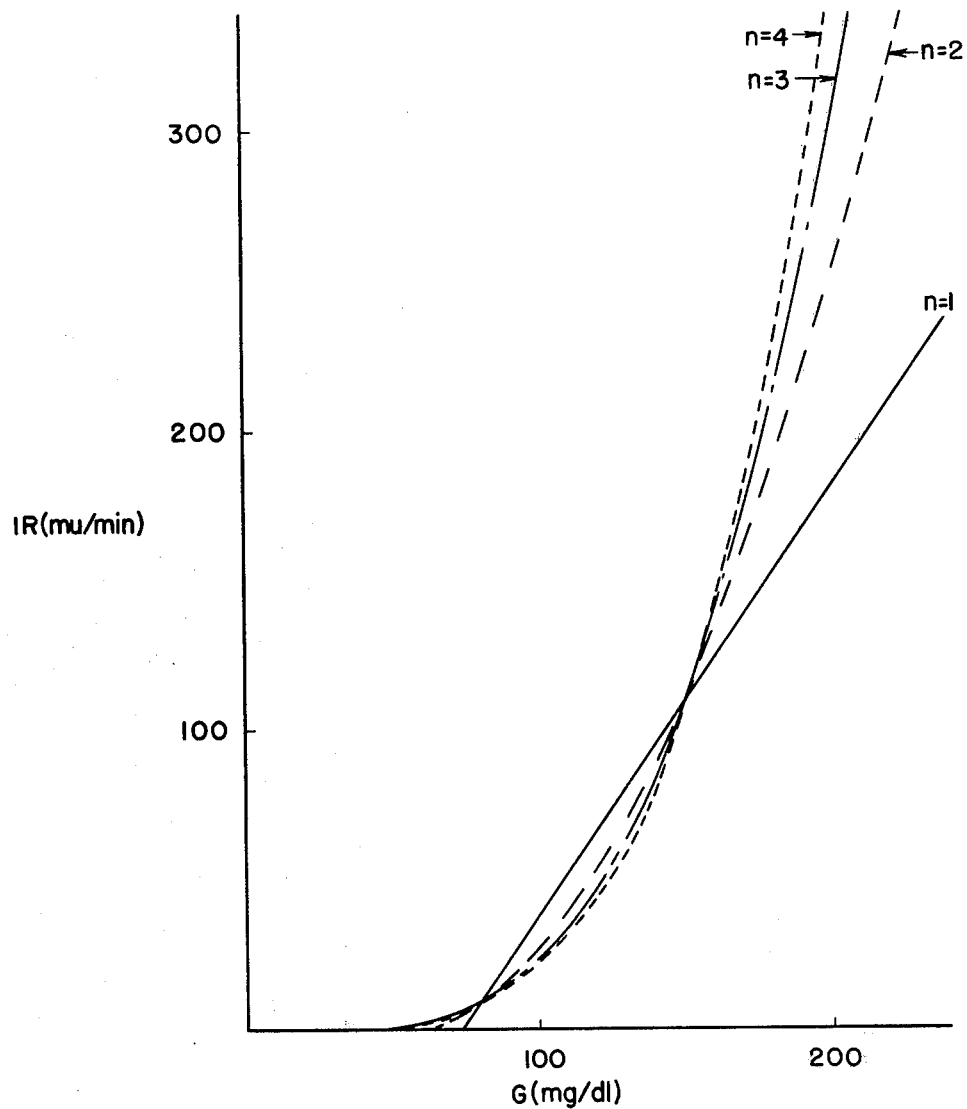
FIG. 2 shows a family of curves representing operation of the apparatus of the present invention in a first control mode contrasted to a curve illustrating insulin infusion rate vs. blood glucose concentration outside the scope of claimed operation.

Typical operating conditions for computer calculated insulin infusion rates (IR) vs. measured serial blood glucose concentrations (G) for the first mode of operation are shown in FIG. 2 and controlled with operating conditions outside the scope of claimed operation. RI and BI are kept constant at typical values of 10 milliunits per minute and 80 mg/dl respectively. QI is maintained at values of 7, 30, 57 and 85 mg/dl for values of n equal to 1, 2, 3 and 4, respectively. The calculated IR is then obtained from the appropriate curve depending on the measured blood glucose reading (G) and the value of n selected by the operator. Comparable curves can also be obtained for different values of n.

Figure 3:
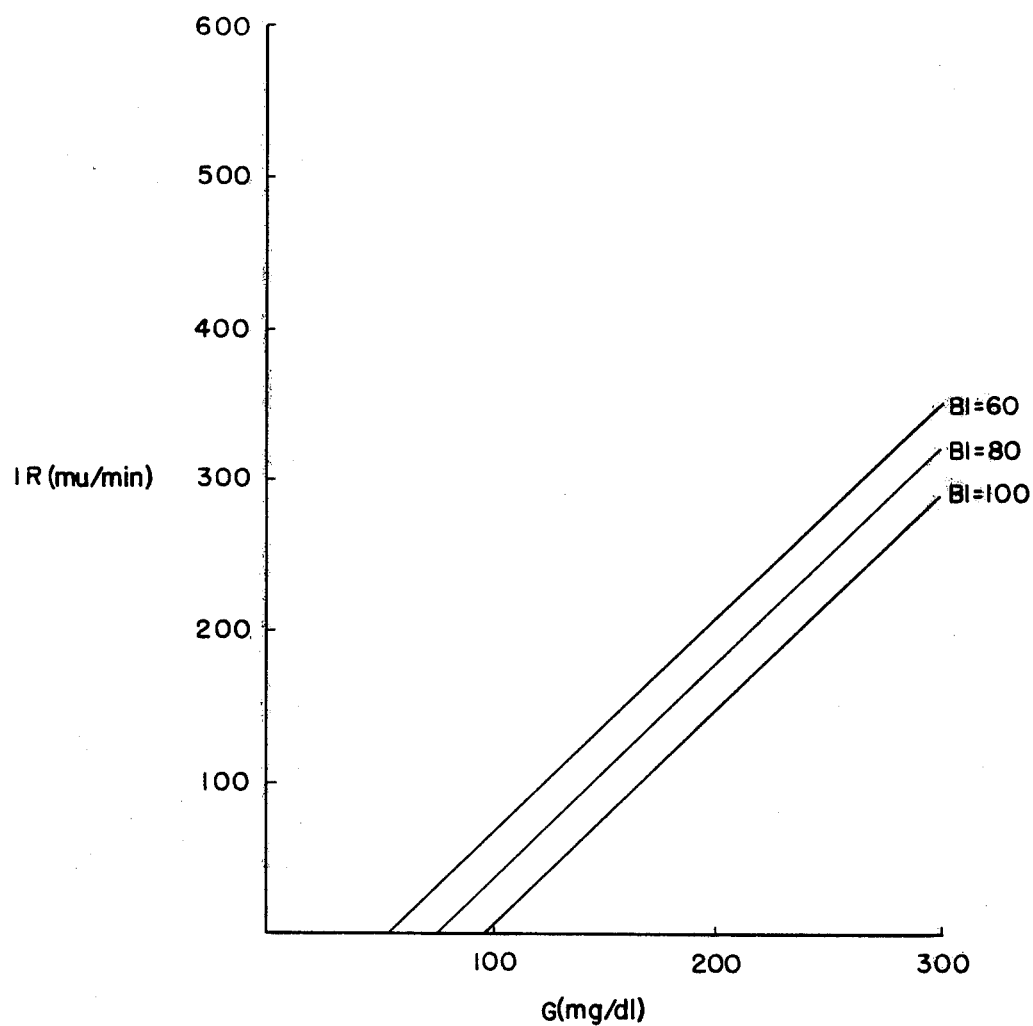
FIGS. 3-5 show families of curves representing operation of the apparatus of the present invention in the first control mode, said curves illustrating insulin infusion rate vs. blood glucose concentration for several basal or steady state glucose concentrations at values of n equal to 1, 2 and 3, respectively.
Figure 4:
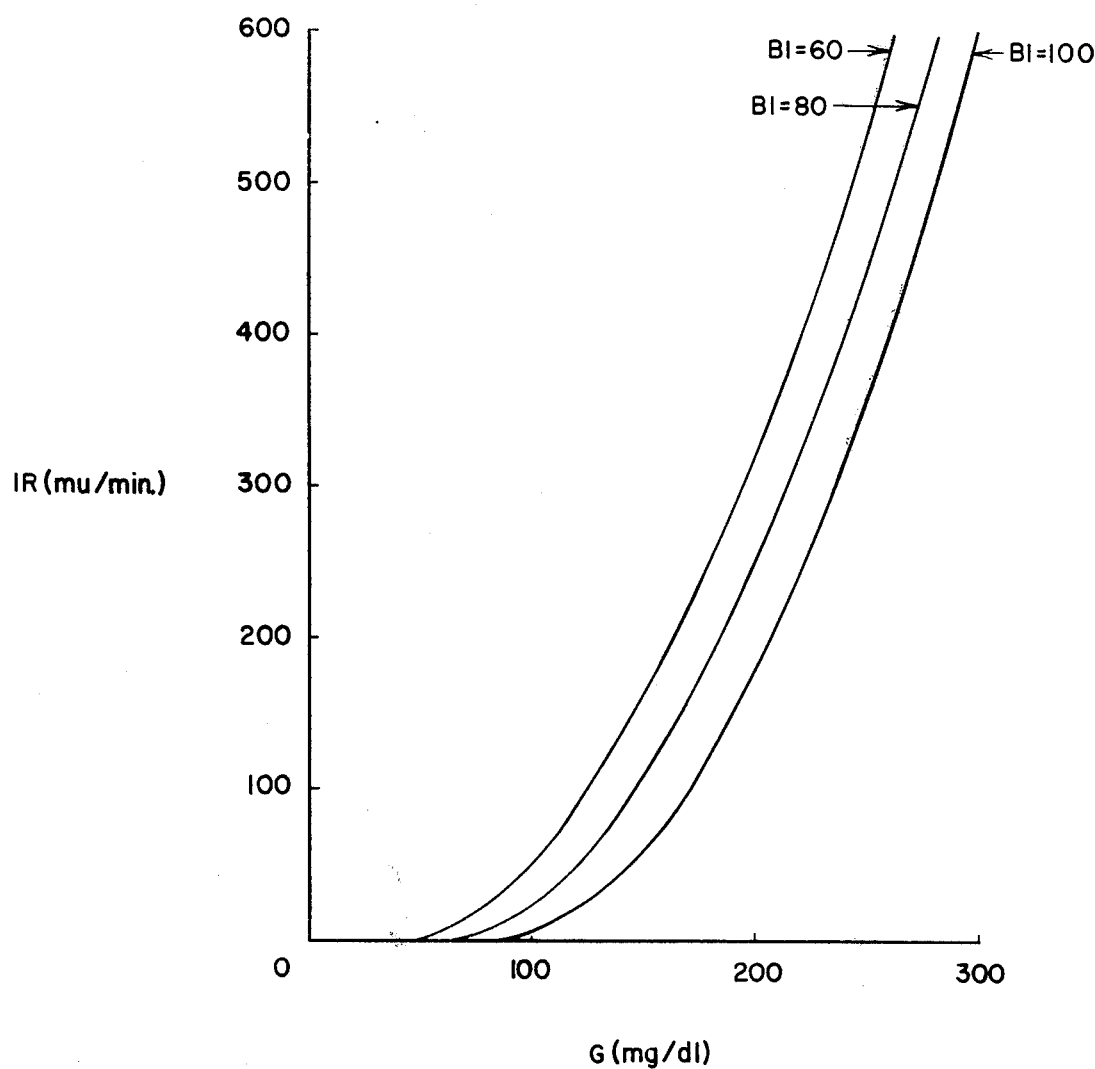
Figure 5:
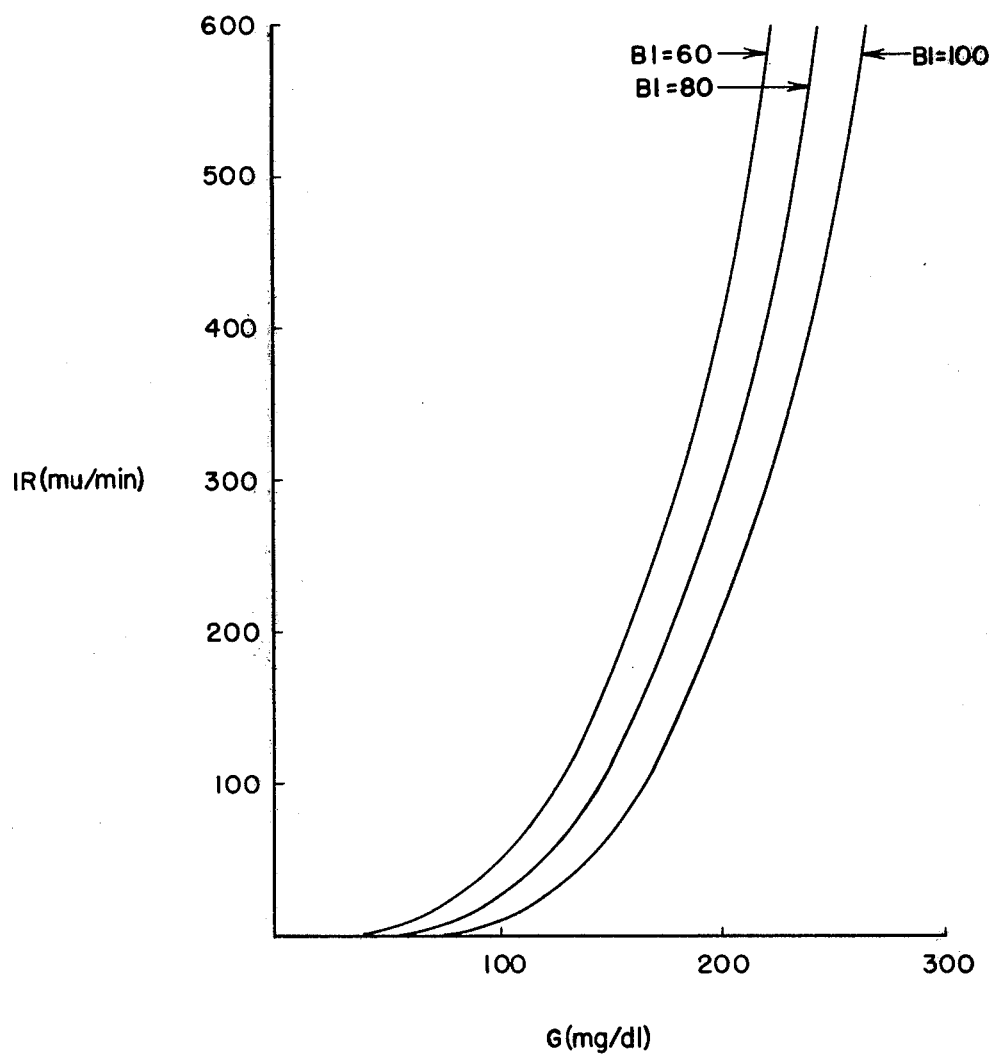

Typical operating conditions for computer calculated insulin infusion rates (IR) vs. measured serial blood glucose concentrations (G) for the first mode of operation are shown in FIGS. 3–5. RI is kept constant at a typical value of 10 mu/min. QI is maintained at 7 mg/dl for n equal to 1, 30 mg/dl for n equal to 2 and 57 mg/dl for n equal to 3. BI is shown for three typical values of 60, 80, and 100 mg/dl. The calculated IR is then obtained from the appropriate curve depending on the measured blood glucose reading (G) and the appropriate BI selected by the operator. Comparable curves can also be obtained for different values of BI.

Figure 6:
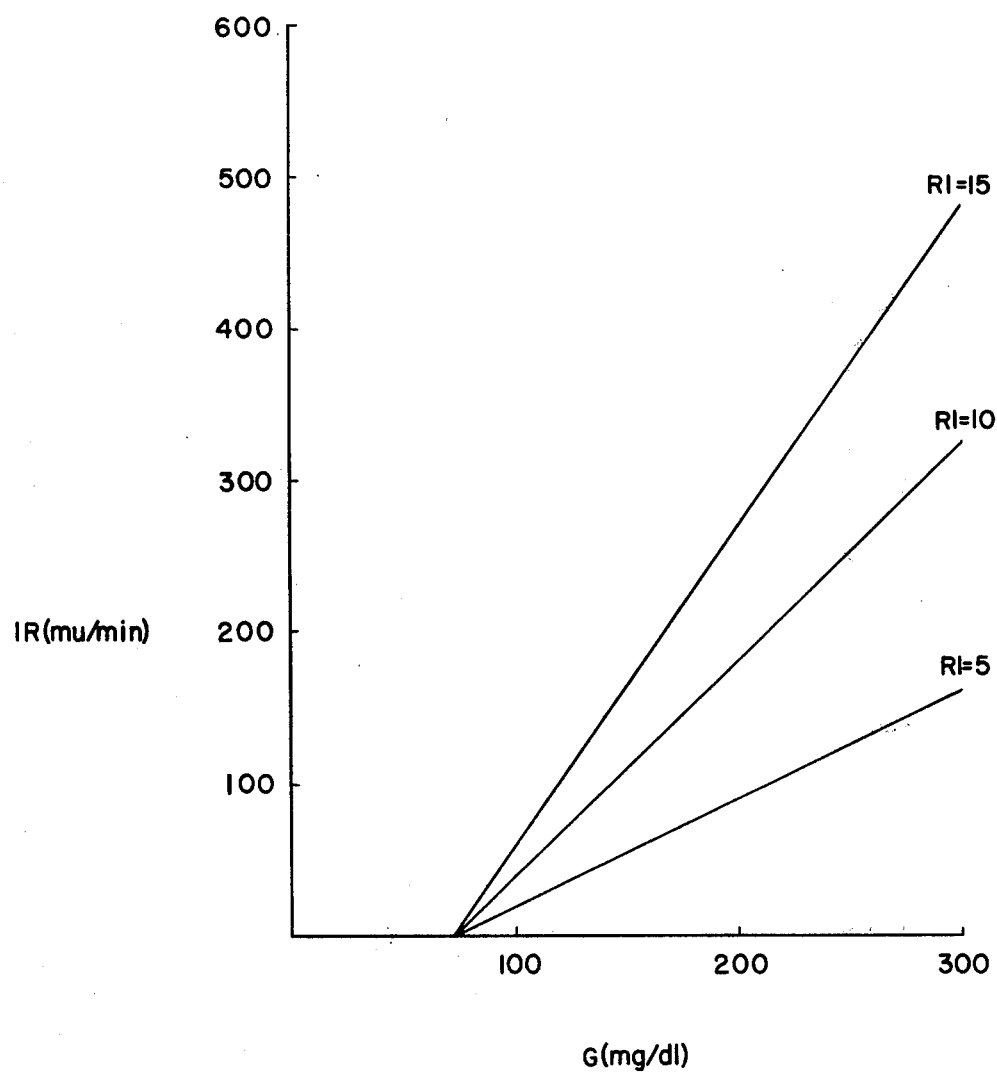
FIGS. 6-8 show families of curves representing operation of the apparatus of the present invention in the first control mode, said curves illustrating insulin infusion rate vs. blood glucose concentration for several required basal infusion rates at values of n equal to 1, 2 and 3, respectively.
Figure 7:
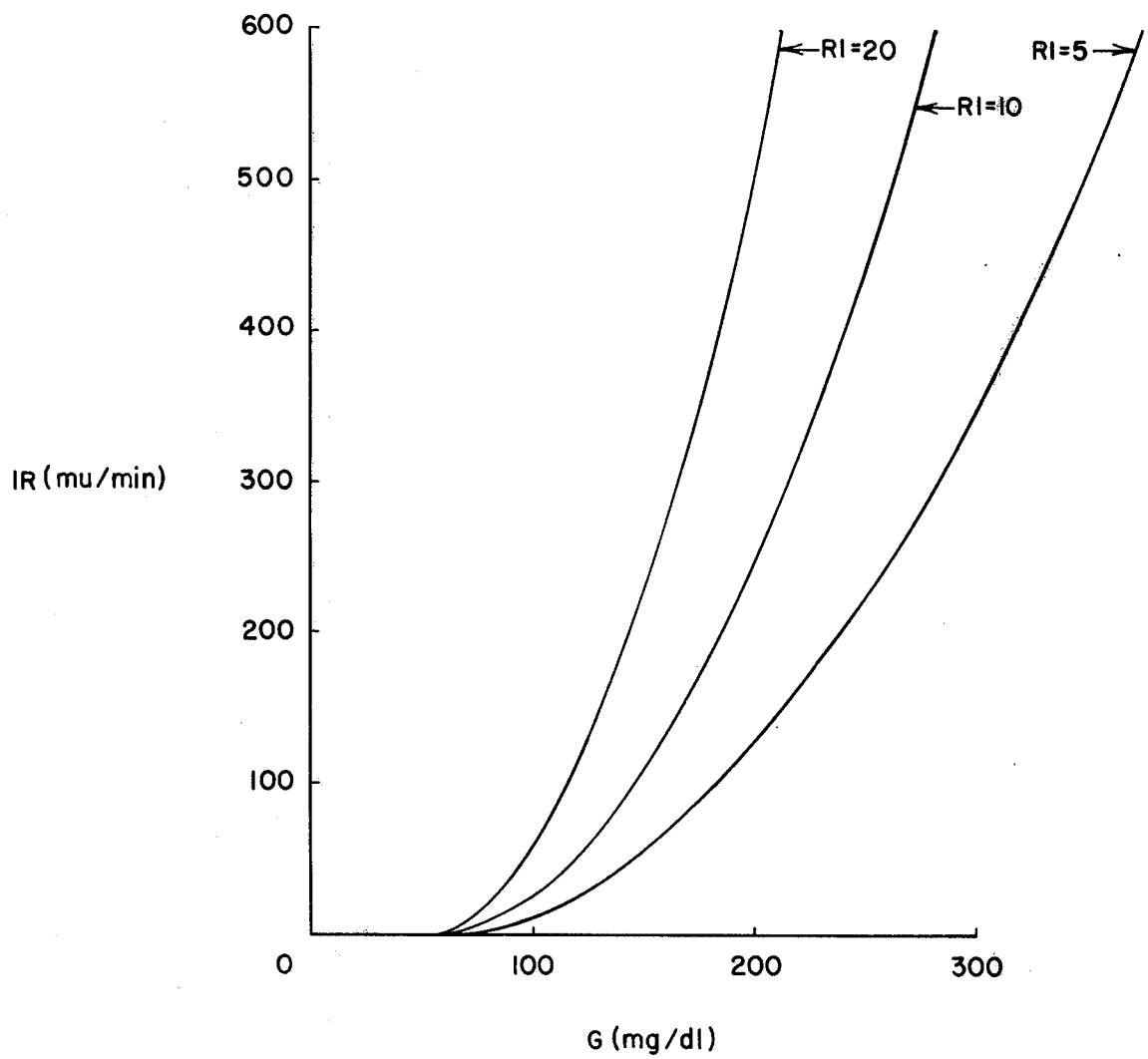
Figure 8:
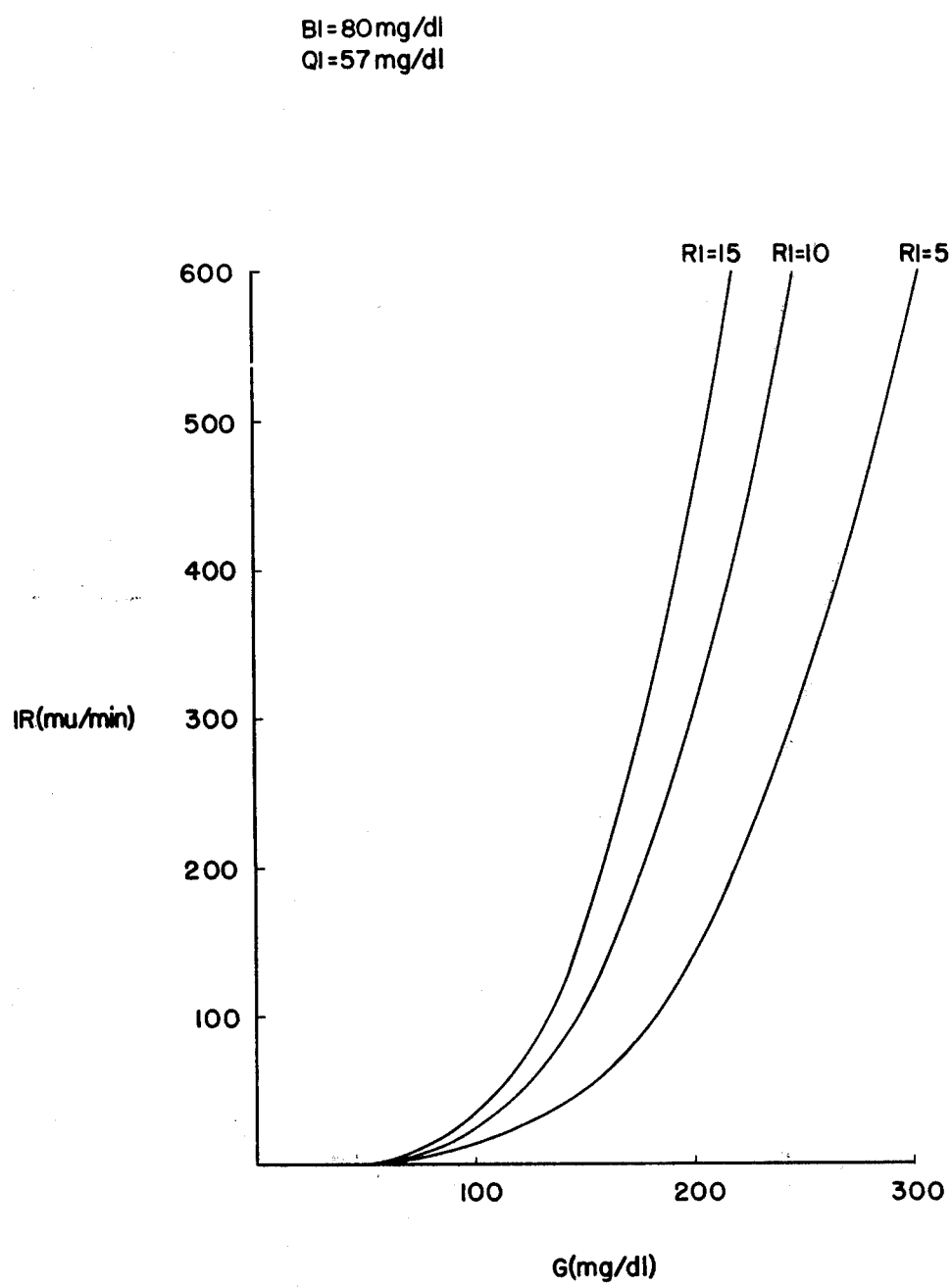

Typical operating conditions for computer calculated insulin infusion rates (IR) vs. measured serial blood glucose concentrations (G) for the first mode of operation are shown in FIGS. 6–8. BI is kept constant at 80 mg/dl. QI is maintained at 7 mg/dl for n equal to 1, 30 mg/dl for n equal to 2 and 57 mg/dl for n equal to 3. RI is shown for three values. The calculated IR is then obtained from the appropriate curve depending on the measured blood glucose reading (G) and the appropriate RI selected by the operator. Comparable curves can also be obtained for different values of RI.

Figure 9:
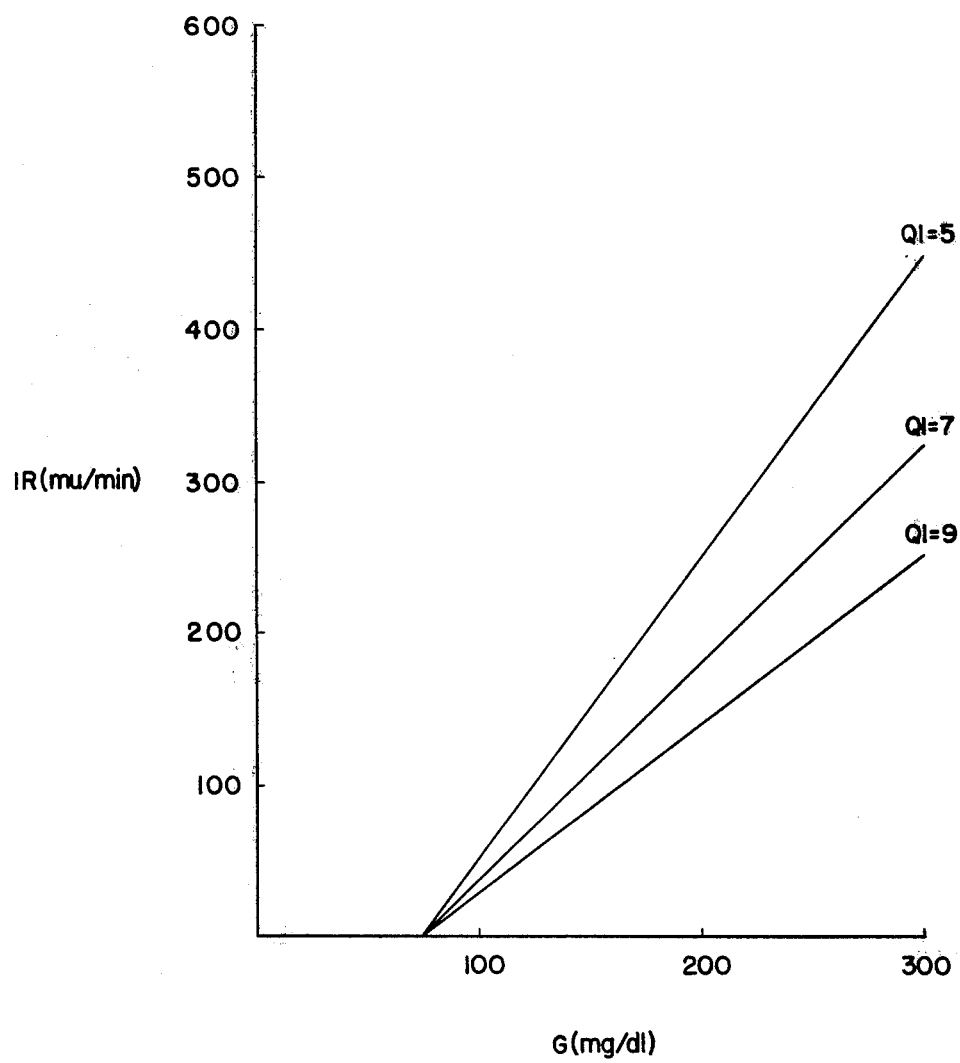
FIG. 9-11 show families of curves representing operation of the apparatus of the present invention in the first control mode, said curves illustrating insulin infusion rate vs. blood glucose concentration for several values of QI at values of n equal to 1, 2, and 3, respectively.
Figure 10:
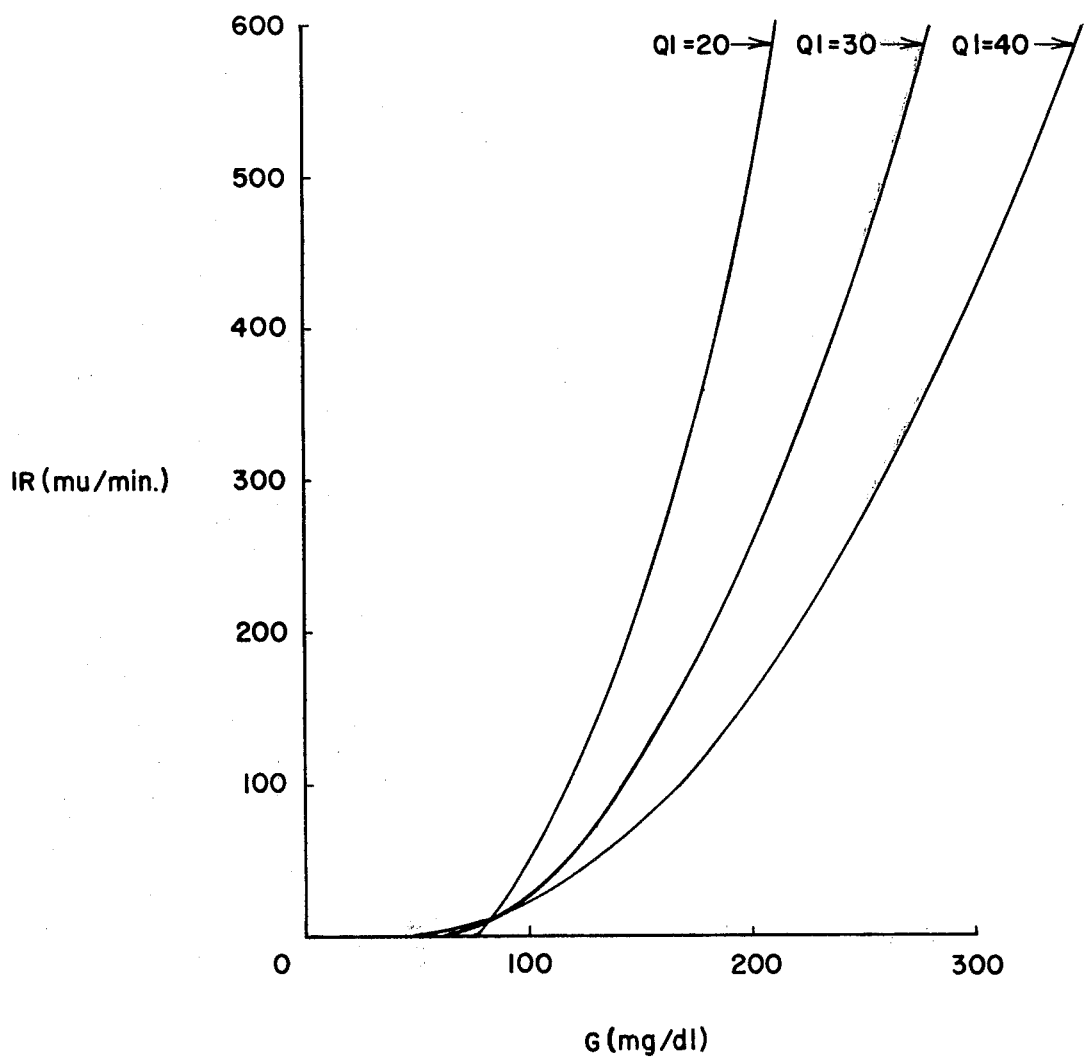
Figure 11:
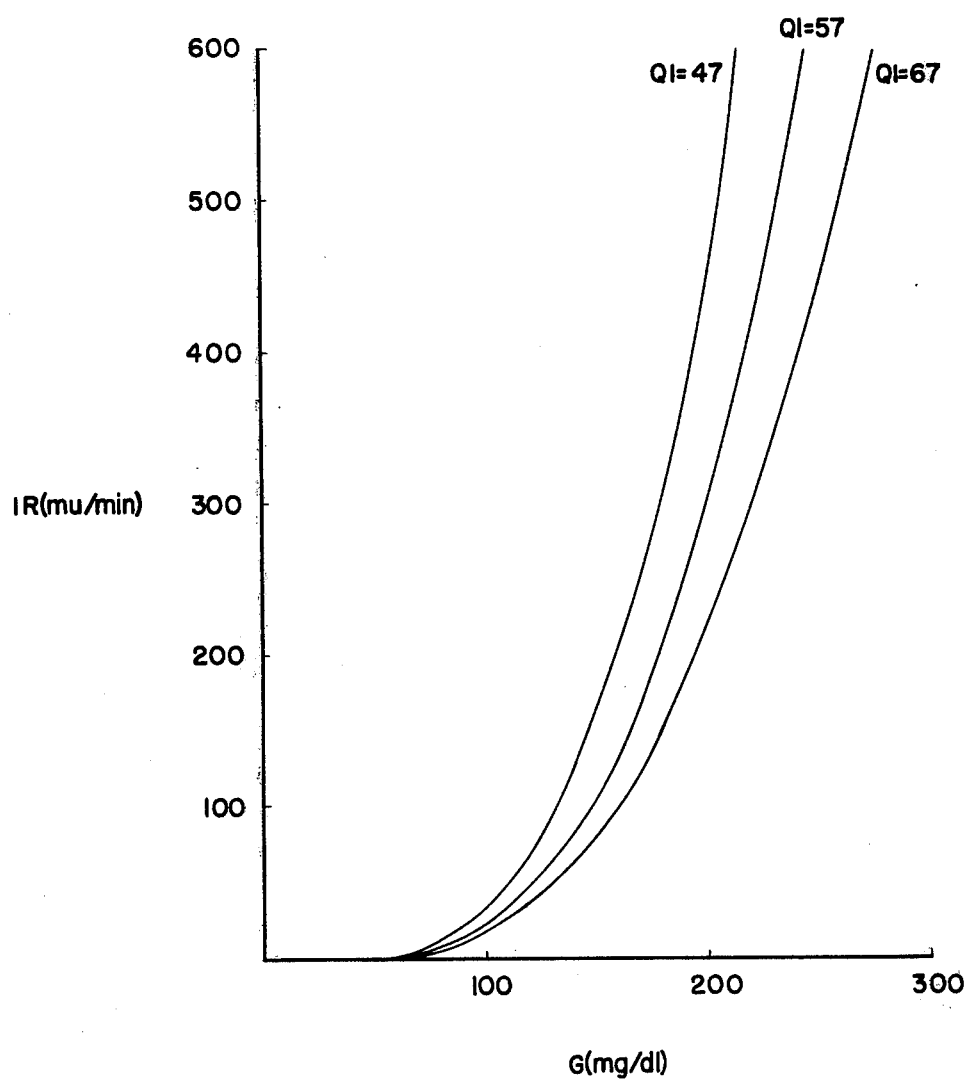

Typical operating conditions for computer calculated insulin infusion rates (IR) vs. measured serial blood glucose concentrations (G) for the first mode of operation are also shown in FIG. 9–11. BI and RI are kept constant at typical values of 80 mg/dl and 10 milliunits per minute, respectively. QI is shown for values of 5, 7 and 9 mg/dl for n equal to 1, 20, 30 and 40 mg/dl for n equal to 2 and 47, 57 and 67 mg/dl for n equal to 3. The calculated IR is then obtained from the appropriate curve depending on the measured blood glucose reading (G) and the appropriate QI selected by the operator. Comparable curves can also be obtained for different values of QI.

Figure 12:
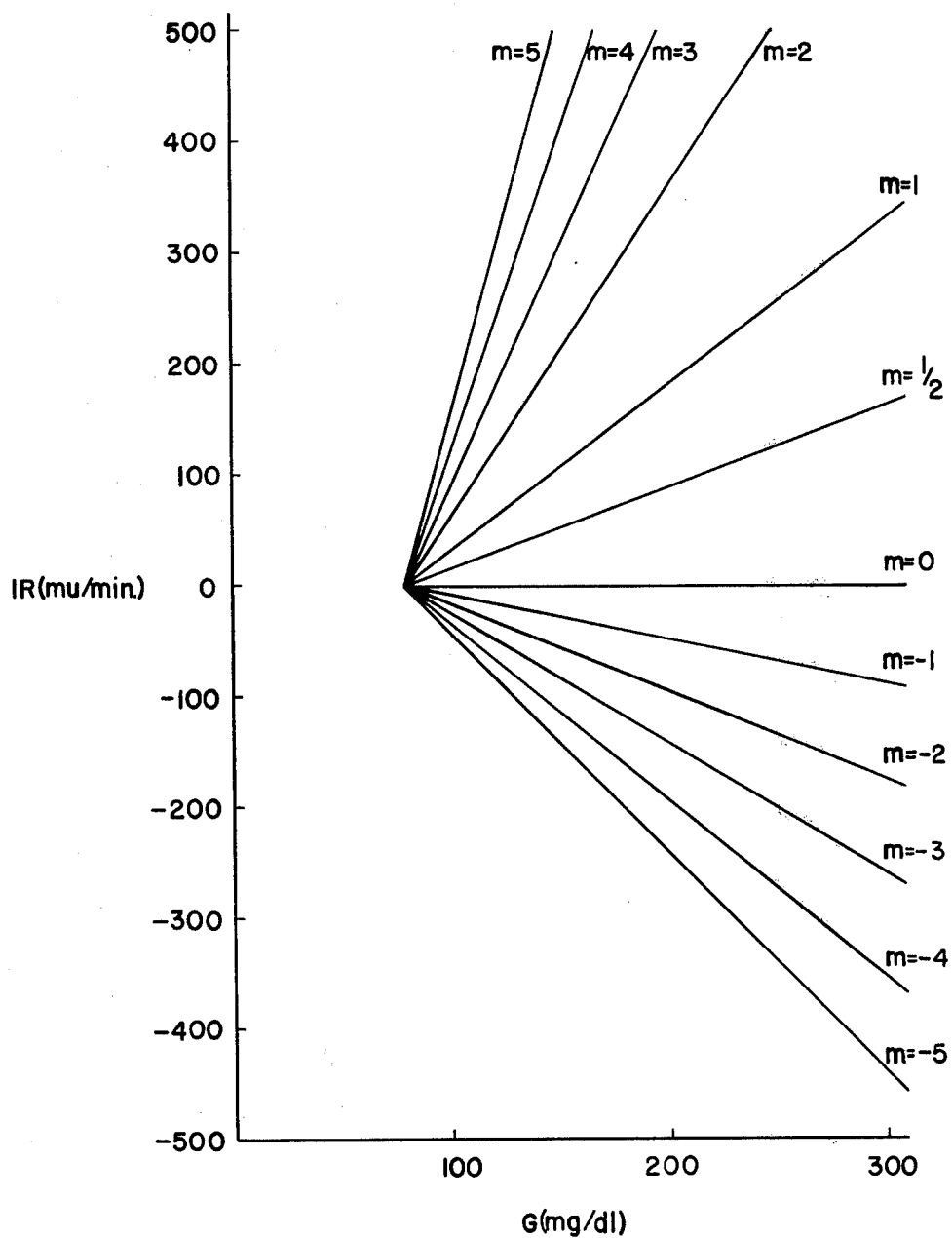
FIGS. 12-14 show families of curves representing operation of the apparatus of the present invention in the second control mode, said curves illustrating insulin infusion rate vs. blood glucose concentration for several values of m at different values of $K_R$ and $K_F$, as defined herein.
Figure 13:
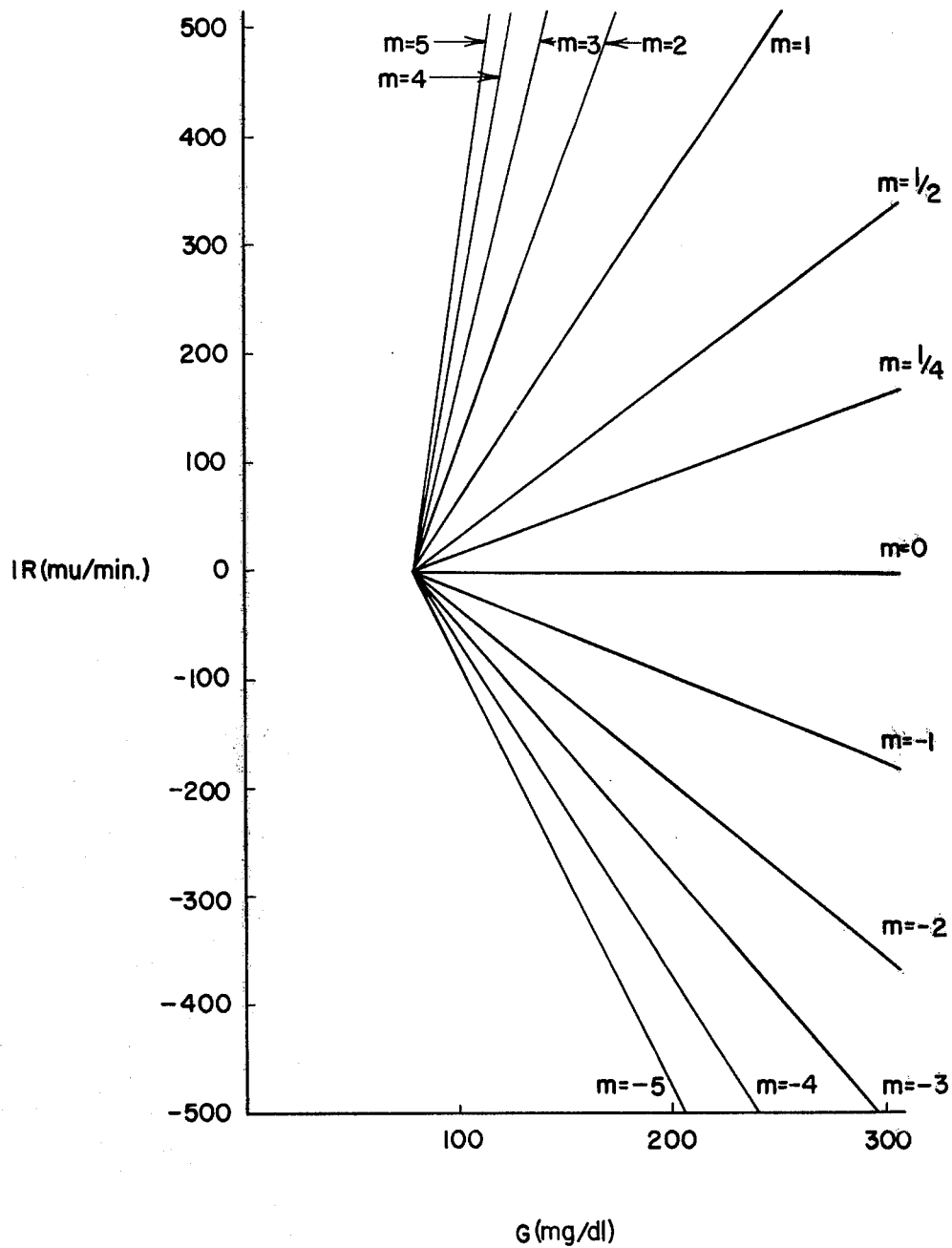
Figure 14:
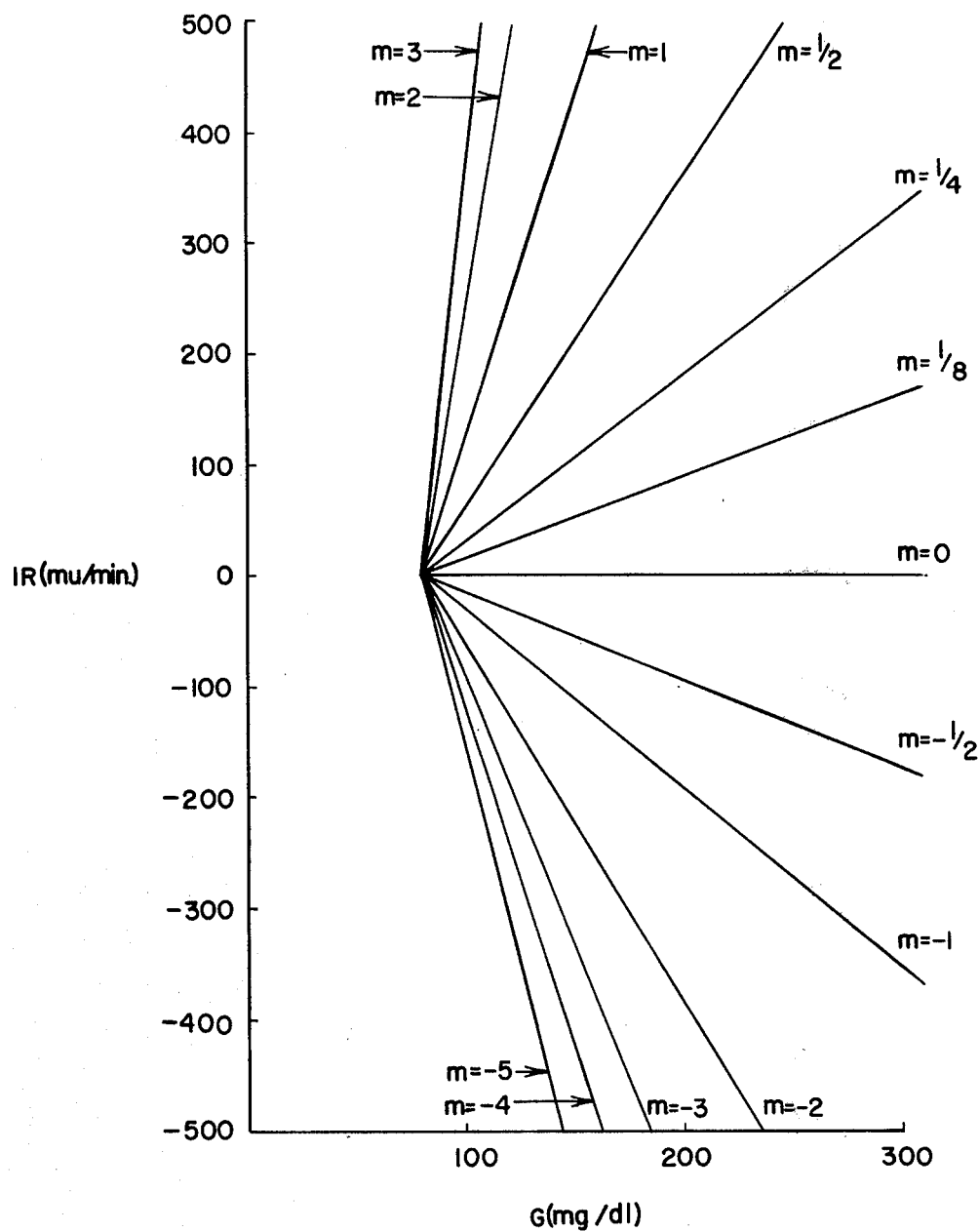

Typical operating conditions for computer calculated insulin infusion rates (IR) vs. measured serial blood glucose concentrations (G) for the second mode of operation plotted for various values of m are shown in FIGS. 12-14. BI is kept constant at 80 mg/dl. The calculated IR is obtained from the appropriate curve depending on the measured blood glucose reading (G) for different values of $K_R$ and $K_F$.

Using the third mode, as described herein, the insulin infusion rate was determined for a human subject. Table I illustrates calculated IR values based on the glucose levels obtained from the human subject. The following preselected values were used:

RI = 18 mu/min,
BI = 80 mg/dl,
QI = 30 mg/dl,
$K_R$ = 30 when the blood glucose concentration of the subject was rising,
$K_F$ = 8 when the blood glucose concentration of the subject was falling based on the expression (Km/10) (Gy − BI)

Table I

| G | IR |
|---|---|
| 100 | 69 |
| 102 | 84 |
| 101 | 85 |
| 101 | 58 |
| 102 | 73 |
| 101 | 50 |
| 101 | 52 |
| 102 | 59 |
| 102 | 60 |
| 102 | 74 |
| 103 | 83 |
| 102 | 61 |
| 104 | 85 |
| 107 | 147 |
| 108 | 191 |
| 107 | 187 |
| 109 | 156 |
| 111 | 154 |
| 112 | 190 |
| 114 | 255 |
| 114 | 218 |
| 113 | 143 |
| 114 | 112 |
| 116 | 126 |
| 116 | 162 |
| 117 | 201 |
| 116 | 114 |
| 115 | 80 |
| 114 | 66 |
| 113 | 52 |
| 110 | 39 |
| 108 | 27 |
| 106 | 19 |
| 107 | 29 |
| 107 | 48 |
| 103 | 41 |
| 101 | 29 |
| 100 | 17 |
| 100 | 22 |
| 101 | 42 |
| 100 | 48 |
| 100 | 50 |
| 100 | 48 |
| 96 | 31 |
| 96 | 26 |
| 96 | 26 |
| 95 | 28 |
| 94 | 33 |
| 94 | 31 |
| 94 | 32 |
| 94 | 36 |
| 93 | 35 |
| 94 | 36 |
| 93 | 35 |
| 93 | 34 |
| 93 | 35 |
| 95 | 47 |
| 92 | 37 |
| 91 | 30 |
| 92 | 28 |

Table I-continued

| G | IR |
|---|---|
| 92 | 28 |

In the apparatus of FIG. 1 any suitable sensor means can be employed to measure the blood glucose concentration of the blood samples obtained from the patient. Likewise any suitable pump can be used in the insulin infusion means. The particular details of sensor 22, computer 28 or pumps 18, 34 and 44 do not form a part of the present invention.

Although not part of the present invention, it will be understood that the apparatus employed to infuse insulin can be used to also infuse glucose when glucose infusion is necessary in order to maintain the desired blood glucose concentration. A suitable algorithm controlling the input of glucose is disclosed in U.S. Ser. No. 685,881, filed May 7, 1976 (now U.S. Pat. No. 4,055,175).

The present apparatus can be designed to provide an alarm when physiological levels have been exceeded. For example, the alarm can function to indicate hypoglycemia or hyperglycemia in a subject. Safeguards, such as means for automatically stopping infusion of insulin under predetermined conditions, can likewise be incorporated, if desired.

From the foregoing, it will be seen that this invention is well adapted to attain all of the ends and objects hereinabove set forth, together with other advantages which are obvious and which are inherent to the system. It can be seen from the above discussion that the apparatus of the present invention provides considerable flexibility to the operator to select not only the specific desired mode of operation, but also to selected desired control values in the computer operating equation for the selected operating mode. The significance of the separation of the various control modes 1, 2 and 3 is especially apparent in the research field. While it is true that the insulin-dependent diabetic requires operating mode 3, the availability of a "pure" derivative control, such as operating mode 2, helps to clarify an important question as to whether "maturity-onset" diabetes is the result of a lacking "first phase" release or a consequence of a reduced number or sensitivity of insulin receptors, or both.

Unlike previous bi-quadratic function algorithms for "static control" mode 1 utilizes an exponential function wherein the exponent can vary from 1 to 3. One advantage of having the algorithm for "static" control as an exponential function in which the exponent varys from 1 to 3 rather than a bi-quadratic function is a reduction in the static gain for the elevated glucose range, an increase in gain in the range immediately above the BI level and a reduction in gain below the BI glucose level. This results in an increase in glucose stabilizing effect of the static control algorithm about the BI glucose level, while concurrently reducing the static insulin release at substantially elevated glucose levels, like severe hyperglycemic conditions. Moreover, the algorithms used avoid one serious shortcoming of earlier algorithms, namely the sensitivity of feedback control output to a "noisy" input signal, particularly noise due to small minute-by-minute analyzer output fluctuations. It will be understood that while preferably the letter "n" in the algorithms of the present invention is the integer 1, 2 or 3, and most preferably 1 or 2, "n" can be any decimal number between 1 and 3.

Obviously, many other modifications and variations of the invention as hereinbefore set forth may be made without departing from the spirit and scope thereof.

What is claimed is:

1. Apparatus for controlling the concentration of glucose in the blood stream of a subject by controlled supply of insulin to such blood stream dependent upon both the concentration of glucose and the rate of change thereof in said blood stream, said apparatus comprising means for determining serial values of blood glucose concentration in the blood steam of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI\left(\frac{G - BI}{QI} + 1\right)^n + K\frac{dG}{dt}$$

wherein:
IR = insulin infusion rate,
RI = required basal infusion rate at BI,
G = the last glucose value,
BI = the desired basal or steady state glucose concentration,
QI = is a preselected value dependent upon the subject,
K = is a preselected value dependent upon the subject and whether or not the blood glucose concentration of the subject is rising ($K_R$) or falling ($K_F$),
t = time; and
n = a number ranging from 1 to 3.

2. Apparatus for controlling the concentration of glucose in the blood stream of a subject by controlled supply of insulin to such blood stream dependent upon both the concentration of glucose and the rate of change thereof in said blood stream, said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said out signals; said computer means being programmed to provide, in response to said input signals, output signals causing said infusion means to introduce insulin to said blood stream at a rate derived in accordance with the equation:

$$IR = RI\left(\frac{Gy - BI}{QI} + 1\right)^n + Km(Gy - BI)$$

except when Gy is less than BI, in which event said rate is derived in accordance with the equation:

$$IR = RI\left(\frac{Gy - BI}{QI} + 1\right)^n$$

wherein:
IR = insulin infusion rate,
RI = required basal infusion rate at BI,
Gy = the last glucose value, corrected to fit a least squares regression line,
BI = the desired basal or steady state glucose concentration,
QI = is a preselected value dependent upon the subject,
K = is a preselected value dependent upon the the subject and whether or not the blood glucose concentration of the subject is rising ($K_R$) or falling; ($K_F$),
m = is the slope of the least squares regression line fit for the most recent consecutive blood glucose values; and
n = a number ranging from 1 to 3.

3. Apparatus for controlling the concentration of glucose in the blood stream of a subject by controlled supply of insulin to such blood stream dependent upon both the concentration of glucose and the rate of change thereof in said blood stream, said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI\left(\frac{G - BI}{QI} + 1\right)^2 + K\frac{dG}{dt}$$

wherein:
IR = insulin infusion rate,
RI = required basal infusion rate at BI,
G = the last glucose value,
BI = the desired basal or steady state glucose concentration,
QI = is a preselected value dependent upon the subject,
K = is a preselected value dependent upon the subject and whether or not the blood glucose concentration of the subject is rising ($K_R$) or falling ($K_F$); and
t = time.

4. Apparatus for controlling the concentration of glucose in the blood stream of a subject by controlled supply of insulin to such blood stream dependent upon both the concentration of glucose and the rate of change thereof in said blood stream, said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said out signals; said computer means being programmed to provide, in response to said input signals, output signals causing said infusion means to introduce insulin to said blood stream at a rate derived in accordance with the equation:

$$IR = RI \left( \frac{Gy - BI}{QI} + 1 \right)^2 + Km(Gy - BI)$$

except when Gy is less than BI, in which event said rate is derived in accordance with the equation:

$$IR = RI \left( \frac{Gy - BI}{QI} + 1 \right)^2$$

wherein:
IR = insulin infusion rate,
RI = required basal infusion rate at BI,
Gy = the last glucose value, corrected to fit a least squares regression line,
BI = the desired basal or steady state glucose concentration,
QI = is a preselected value dependent upon the subject,
K = is a preselected value dependent upon the the subject and whether or not the blood glucose concentration of the subject is rising ($K_R$) or falling ($K_F$); and
m = is the slope of the least squares regression line fit for the most recent consecutive blood glucose values.

5. Apparatus for controlling the concentration of glucose in the blood stream of a subject by controlled supply of insulin to such blood stream dependent upon the concentration of glucose in said blood stream, said apparatus comprising means for determining serial values of blood glucose concentrations in the blood stream of a subject and for providing computer input signals corresponding to said serial values, computer means connected to said first mentioned means and operable to provide output signals in response to said input signals; and infusion means connected to said computer means and to a source of insulin and responsive to said output signals for introducing insulin from said course to said blood stream at a rate determined by said output signals; said computer means being programmed to provide, in response to said input signals, output signals causing said infusion means to introduce insulin to said blood stream at a rate derived in accordance with the equation:

$$IR = RI \left( \frac{G - BI}{QI} + 1 \right)$$

wherein:
IR = the insulin infusion rate,
RI = the desired basal insulin infusion rate at BI,
G = the last glucose value,
BI = the desired basal or steady state glucose concentration, and
QI = a preselected value depending upon the subject.

6. Apparatus for controlling the concentration of glucose in the blood stream of a subject by controlled supply of insulin to such blood stream dependent upon the concentration of glucose in said blood stream, said apparatus comprising means for determining serial values of blood glucose concentrations in the blood stream of a subject and for providing computer input signals corresponding to said serial values, computer means connected to said first mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI \left( \frac{G - BI}{QI} + 1 \right)^2 \text{ wherein:}$$

wherein:
IR = the insulin infusion rate,
RI = the required basal insulin infusion rate at BI,
G = the last glucose value,
BI = the desired basal or steady state glucose concentration, and
QI = a preselected value depending upon the subject.

7. Apparatus for controlling the concentration of glucose in the blood stream of a subject by controlled supply of insulin to such blood stream dependent upon the concentration of glucose in said blood stream, said apparatus comprising means for determining serial values of blood glucose concentrations in the blood stream of a subject and for providing computer input signals corresponding to said serial values, computer means connected to said first mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI \left( \frac{G - BI}{QI} + 1 \right)^3$$

wherein:
IR = the insulin infusion rate,
RI = the required basal insulin infusion rate at BI,
G = the last glucose value,
BI = the desired basal or steady state glucose concentration, and
QI = a preselected value depending upon the subject.

8. Apparatus for controlling the concentration of glucose in the blood stream of a subject by controlled supply of insulin to such blood stream dependent upon the concentration of glucose in said blood stream, said apparatus comprising means for determining serial values of blood glucose concentration in the blood stream of a subject and for providing computer input signals corresponding to said serial values; computer means connected to said first mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI\left(\frac{Gy - BI}{QI} + 1\right)$$

wherein:
- IR = the insulin infusion rate,
- RI = the required basal insulin infusion rate at BI,
- Gy = the last glucose value, corrected to fit a least squares regression line,
- BI = the desired basal or steady state glucose concentration, and
- QI = a preselected value depending upon the subject.

9. Apparatus for controlling the concentration of glucose in the blood stream of a subject by controlled supply of insulin to such blood stream dependent upon the concentration of glucose in said blood stream, said apparatus comprising means for determining serial values of blood glucose concentration in the blood stream of a subject and for providing computer input signals corresponding to said serial values; computer means connected to said first mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI\left(\frac{Gy - BI}{QI} + 1\right)^2$$ wherein:

wherein:
- IR = the insulin infusion rate,
- RI = the required basal insulin infusion rate at BI,
- Gy = the last glucose value, corrected to fit a least squares regression line,
- BI = the desired basal or steady state glucose concentration, and
- QI = a preselected value depending upon the subject.

10. Apparatus for controlling the concentration of glucose in the blood stream of a subject by controlled supply of insulin to such blood stream dependent upon the concentration of glucose in said blood stream, said apparatus comprising means for determining serial values of blood glucose concentration in the blood stream of a subject and for providing computer input signals corresponding to said serial values; computer means connected to said first mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = RI\left(\frac{Gy - BI}{QI} + 1\right)^3$$

wherein:
- IR = the insulin infusion rate,
- RI = the required basal insulin infusion rate at BI,
- Gy = the last glucose value, corrected to fit a least squares regression line,
- BI = the desired basal or steady state glucose concentration, and
- QI = the preselected value depending upon the subject.

11. Apparatus for controlling the concentration of glucose in the blood stream of a subject by controlled supply of insulin to such blood stream dependent upon the rate of change of glucose concentration in said blood stream, said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = K(dG/dt)$$

wherein:
- IR = the insulin infusion rate,
- K = a preselected value dependent upon the subject and whether or not the blood glucose concentration of the subject is rising ($K_R$) or falling ($K_F$),
- G = the last glucose value, and
- t = time.

12. Apparatus for controlling the concentration of glucose in the blood stream of a subject by controlled supply of insulin to such blood stream dependent upon the rate of change of glucose concentration in said blood stream said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said output signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = Km$$

wherein:
- IR = the insulin infusion rate,
- K = a preselected value dependent upon the subject and whether or not the blood glucose concentration of the subject is rising ($K_R$) or falling ($K_F$), and
- M = the slope of the least squares regression line fit for the most recent consecutive glood glucose values.

13. Apparatus for controlling the concentration of glucose in the blood stream of a subject by controlled supply of insulin to such blood stream dependent upon the rate of change of glucose concentration in said blood stream said apparatus comprising means for determining serial values of blood glucose concentration in the blood stream of a subject and for providing computer input signals corresponding to said serial values; computer means connected to said first-mentioned means and operable to provide output signals in response to said input signals; and infusion means connected to said computer means and to a source of insulin and responsive to said out signals for introducing insulin from said source to said blood stream at a rate determined by said output signals; said computer means being programmed to provide, in response to said input signals, output signals causing said infusion means to introduce insulin to said blood stream at a rate derived in accordance with the equation:

$$IR = Km(Gy - BI)$$

except when GY is less than BI, in which event IR equals zero,
wherein:
IR = the insulin infusion rate,
K = a preselected value dependent upon the subject and whether or not the blood glucose concentration of the subject is rising ($K_R$) or falling ($K_F$),
m = the slope of the least squares regression line fit for the most recent consecutive blood glucose values,
Gy = the last glucose value, corrected to fit a least squares regression line, and
BI = the desired basal or steady state glucose concentration.

* * * * *